United States Patent [19]

Takagi et al.

[11] Patent Number: 4,942,619
[45] Date of Patent: Jul. 17, 1990

[54] PATTERN INSPECTING APPARATUS

[75] Inventors: Makoto Takagi, Kawasaki; Norio Fujii, Urawa; Yoshihiko Fujimori, Tokyo, all of Japan

[73] Assignee: Nikon Corporation, Tokyo, Japan

[21] Appl. No.: 289,428

[22] Filed: Dec. 23, 1988

Related U.S. Application Data

[63] Continuation of Ser. No. 3,245, Jan. 14, 1987, abandoned.

[30] Foreign Application Priority Data

Jan. 20, 1986 [JP] Japan ................................ 61-10675
May 23, 1986 [JP] Japan ............................... 61-118831

[51] Int. Cl.$^5$ .............................................. G06K 9/42
[52] U.S. Cl. ......................................... 382/47; 382/8; 382/30
[58] Field of Search ...................... 382/47, 27, 30, 8; 340/731

[56] References Cited

U.S. PATENT DOCUMENTS 4,414,685 11/1983 Sternberg .............................. 382/27
4,481,664 11/1984 Linger .................................... 382/8
4,641,350 2/1987 Bunn ...................................... 382/30
4,725,892 2/1988 Suzuki .................................... 382/47

OTHER PUBLICATIONS

"Special Purpose Hardware for Design Rule Checking," Larry Seiler, Feb. 1981.

Primary Examiner—Leo H. Boudreau
Assistant Examiner—Joseph Mancuso
Attorney, Agent, or Firm—Shapiro and Shapiro

[57] ABSTRACT

A pattern inspection apparatus for accurately inspecting a pattern such that design image data is processed in correspondence to resizing of a pattern to be inspected. Image data corresponding to an image area of a predetermined size is extracted from input information represented by binary logic levels and representing a pattern to be resized. Template circuits add additional data of a predetermined logic level to a predetermined pixel position when a distribution of the image logic levels included in the extracted image data is a predetermined distribution. Thus, the additional data is added to the pattern image data to resize the pattern.

5 Claims, 7 Drawing Sheets

PATTERN INSPECTING APPARATUS

This is a continuation application of Ser. No. 003,245 filed Jan. 14, 1987, now abandoned.

BACKGROUND OF THE INVENTION

1. Field of the Invention

The present invention relates to an inspecting apparatus utilizing a pattern recognition technique and, more particularly, to an apparatus suitably applied to enlarging or reducing each pattern size in binary image information.

2. Related Background Art

In a semiconductor fabrication apparatus, a pattern to be projected onto a semiconductor wafer is formed beforehand on a reticle. In order to inspect whether the pattern on the reticle has a predetermined size or whether scratches and unnecessary indentations are present in the pattern, the pattern on the reticle is picked up by an image pick-up device, and signal levels of pixels constituting a planar pattern are converted into binary data signals. The detected binary data is compared with reference data representing a reference pattern.

When the reticle pattern is inspected according to the above technique and the reticle pattern size is slightly different from the predetermined reference pattern, a defect present in the reticle pattern often cannot be properly be detected upon comparison between the detected binary data and the reference data, and the entire pattern is often detected as defective. In order to eliminate this drawback, the reference pattern must be enlarged or reduced, so as to be matched with the pattern to be inspected.

When a reticle pattern is designed in practice, individual pattern sizes are selected on the basis of a common reference pattern so as to comply with the fabrication steps of semiconductors to be fabricated. In this manner, a pattern having an optimal size must be used to form an identical pattern on a reticle or a mask. In this case, the pattern size must be controlled to derive a size of a pattern to be formed on the reticle or mask from the reference design pattern.

For this purpose, a typical conventional pattern processor is proposed wherein positional image information is generally produced by a computer and stored in an external memory, and the stored data is read out at the time of creation of a desired reticle pattern, thereby obtaining an image signal for forming the reticle pattern.

In order to enlarge or reduce the size of the pattern according to the above method the computer must perform arithmetic operations or binary image data for all patterns according to an enlargement or reduction ratio, thus undesirably requiring long processing time.

SUMMARY OF THE INVENTION

It is an object of the present invention to provide an apparatus for accurately inspecting a pattern such that design image data is processed in correspondence to resizing of a pattern to be inspected.

It is another object of the present invention to provide a pattern resizing apparatus capable of greatly shortening processing time when a pattern represented by image information is resized as needed.

The apparatus of the present invention comprises means for extracting image data corresponding to an image area of a predetermined size from input information represented by binary logic levels and representing a pattern to be resized, and template means for adding additional data of a predetermined logic level to a predetermined pixel position when a distribution of the image logic levels included in the extracted image data is a predetermined distribution. Thus, the additional data is added to the pattern image data to resize the pattern.

The binary input information is extracted by the image data extracting means to have an image area of a predetermined size (e.g., 9×9 pixels). The extracted image data is then input to the template means.

The template means discriminates whether the distribution of the logic levels of pixels included in the image data is a predetermined distribution. If the predetermined distribution is detected, the additional data of the predetermined logic level is added to the predetermined pixel position. Discrimination of the distribution of the logic levels is performed in units of pixels as follows. Each pixel is compared with the reference distribution. If a pixel included in the image data has a logic level matching with the logic level constituting the reference distribution, the additional data is added to the predetermined pixel position.

Data for enlarging or reducing the size of each pattern is added to image data at a position spaced by a distance between the position of the pixel whose logic level coincides with that of the reference distribution and the position of the pixel added with the additional data.

With the above arrangement, long processing time of the computer is not required, and sizes of individual patterns can be easily resized with simple hardware.

DESCRIPTION OF THE PREFERRED EMBODIMENTS

Figure 1:
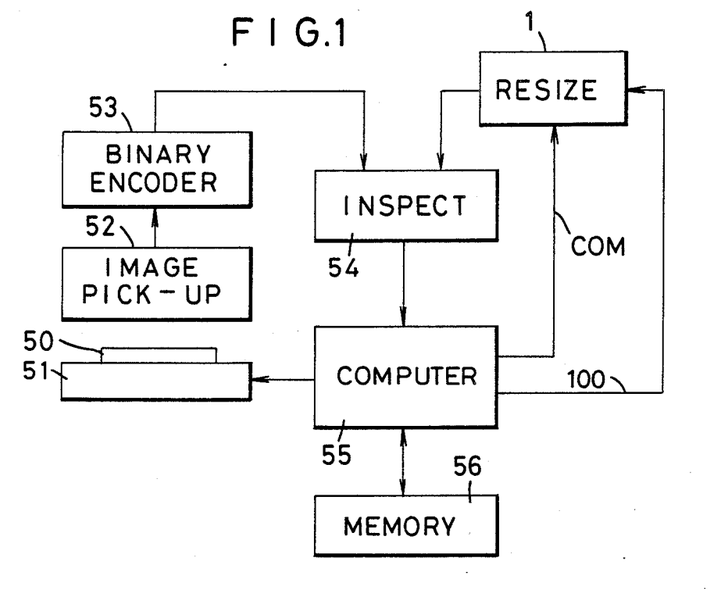
FIG. 1 is a block diagram showing a pattern inspecting apparatus according to the present invention.

FIG. 1 is a block diagram of a pattern inspecting apparatus according to the present invention. An object 50 to be inspected, such as a reticle or a mask which has a pattern formed on the basis of design information and to be inspected, is placed on a stage 51. A pattern to be inspected and included in a small area as part of the entire pattern to be inspected is picked up by an image pick-up device 52 including a one-dimensional image pick-up element. In this case, the object 50 is moved on the stage 51 along one direction, and at the same time, the image pick-up device 52 is scanned in a direction perpendicular to the moving direction of the stage 51. Analog image information from the image pick-up device 52 is output to a binary encoder 53. The binary encoder 53 samples the analog image information 512 times per scanning line of the image pick-up device 52. The sampled analog image information levels are converted into binary signals, thereby obtaining binary image information. The binary image information is time-serial image data of 512×N pixels (where N is a value changing depending on the moving distance of the stage and the scanning interval of the image pick-up device). Each pixel represented by the image data is represented by logic "1" (a chromium pattern portion) or logic "0" (a nonpattern portion). The resultant image data is output to an inspecting circuit 54.

A computer 55 reads out reference image data from an external memory 56. The reference image data corresponds to a small local area of the pattern to be inspected and read by the image pick-up device 52. The readout data is output to a resize circuit 1. The resize circuit 1 processes the reference image data read out under the control of the computer 55. A reference pattern represented by the image data is enlarged or reduced, and the processed data is sent to the inspecting circuit 54.

The inspecting circuit 54 compares the image information and the reference image data, both of which are time-serially input and synchronized with each other. If a difference between the input image information and the reference image data is detected as a defect of the pattern to be inspected, defect data is sent to be computer 55. The computer 55 sends the defect data to the external memory 56, and the sent data is stored.

The computer 55 controls the associated components for optimally performing defect inspection. For example, the computer 55 produces a drive control signal for the stage 51 and a command signal COM for controlling the resizing of the pattern resize circuit 1.

Figure 2:
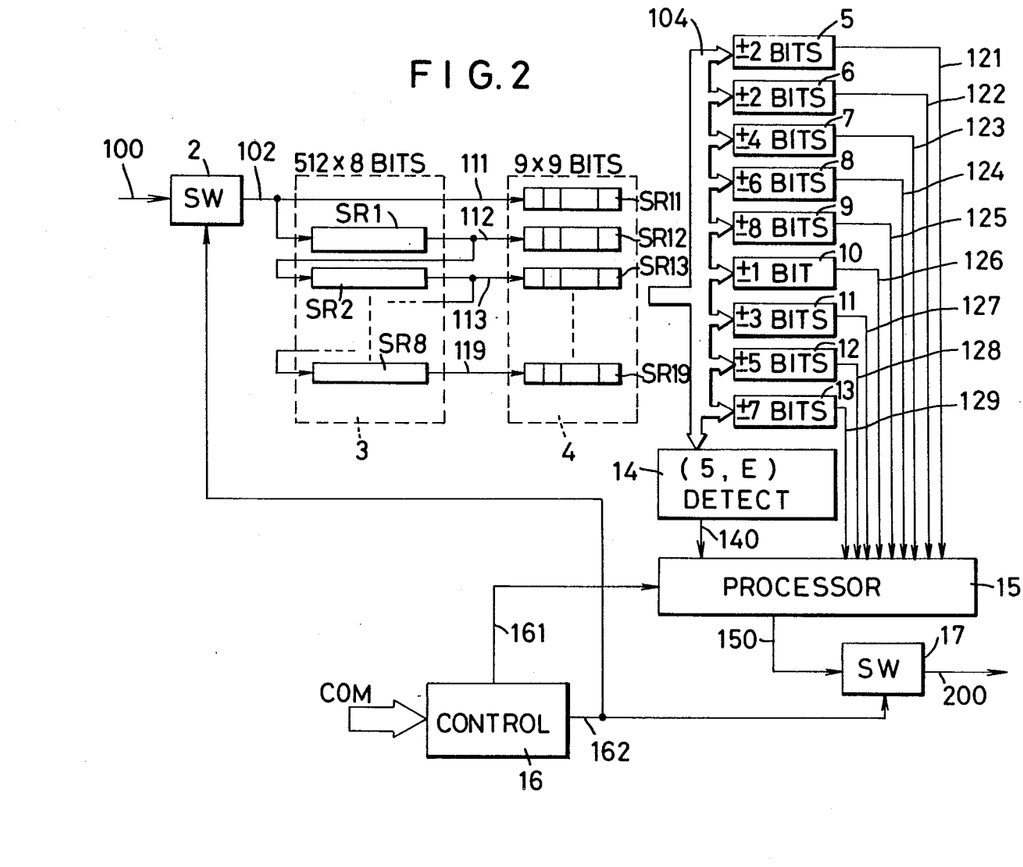
FIG. 2 is a block diagram showing an embodiment of a pattern resize circuit.

The pattern resize circuit 1 is arranged, as shown in FIG. 2. One-bit reference image information 100 representing a pattern to be resized is serially sent to a pattern memory section 3 through a switching circuit 2. The reference image information 100 consists of raster image data having data of 512 pixels per horizontal scanning line SC. Reference image information 102 consisting of the pixel data of logic "1" or "0" and constituting a pattern image PT is serially stored in the pattern memory section 3 in response to a sync signal.

In this embodiment, the pattern memory section 3 has a 512-bit arrangement of series-connected shift registers SR1, SR2, ... SR8 of a serial input-serial output type. The pattern memory section 3 does not process the reference image information 102 input from the switching circuit 2 and outputs it as first output information 111. At the same time, binary image information signals appearing at the output terminals of the registers SR1, SR2, ... SR8 are sent as second output information 112, third output information 113, ... ninth output information 119.

The pattern memory section 3 simultaneously sends 9-line pattern information, i.e., pattern image information 111, pattern image information 112, ... pattern image information 119 to corresponding shift registers SR11, SR12, ... SR19 in an extraction section 4.

The shift registers SR11, SR12, ... SR19 in the extraction section 4 comprise 9-1 bit serial-input parallel-output shift registers, respectively. The storage contents of the bits (i.e., data of 81 (=9×9) pixels) are output as parallel local image data 104. The extraction section 4 is operated such that the pixel data stored in the pattern memory section 3 is extracted in units of local rectangular areas each consisting of 9×9 pixels.

Figure 3A:
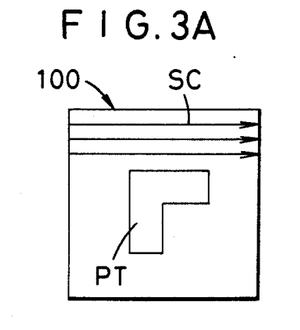
FIGS. 3A and 3B are views for explaining the extraction operations of an extraction section.
Figure 3B:
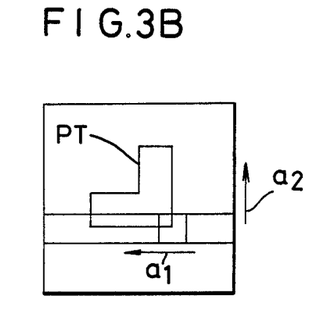

When pixel data is supplied to the pattern memory section 3 in such an order that the pixel data is scanned along the scanning line SC of the reference image information 102 in FIG. 3A, the pattern memory section 3 rotates through 180° the pattern PT consisting of pixel data represented by the reference image information 102 and stores the reordered data therein. The extraction section 4 uses the local rectangular area of 9×9 pixels as a window and sequentially extracts the pixel data of the rotated pattern PT along the horizontal direction indicated by an arrow a1 in FIG. 3B. This extraction scanning is repeated whenever the scanning position is shifted by one pixel along the vertical direction indicated by an arrow a2.

Figure 4:
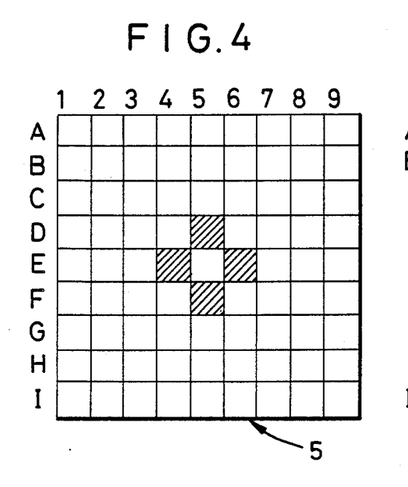
FIGS. 4, 5, 6, 7, 8, 9, 10, 11 and 12 show template circuits 5, 6, 7, 8, 9, 10, 11, 12 and 13 respectively.

In order to specify a given pixel included in the local rectangular area constituted by 9×9 pixels, x-coordinates and y-coordinates (the number of lines, the number of columns) of the pixels in the local rectangular area are represented by numbers 1 to 9 and letters A to I, respectively, as shown in FIG. 4 and thereafter. For example, the pixel at the upper left corner is represented by point (1,A).

The local image data 104 thus extracted is sent to nine template circuits 5 to 13 and a detector 14 for extracting the original image data.

The 2-pixel width resize template circuit 5 receives four pixel data represented by the hatched squares, i.e., points (5,D), (4,E), (6,E) and (5,F) out of the extracted local image data 104, as shown in FIG. 4, and performs an arithmetic operation on the four pixel data. The template circuit 5 then outputs the calculated result. In this case, the arithmetic operation is a logical OR product More specifically, if at least one of the input pixel signals is set at logic "1", the template circuit 5 outputs additional data of logic "1". Referring to FIG. 4, each time the reference image information of logic "1" is input to a position corresponding to point (5,D), (4,E), (6,E) or (5,F), an output 121 of logic "1" appears at the output terminal of the template circuit 5. The output 121 is then sent to a processor 15.

Figure 5:
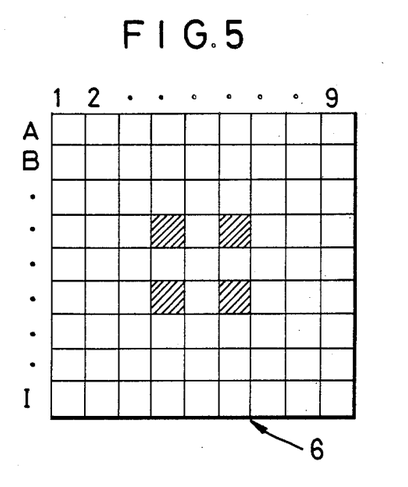

As shown in FIG. 5, another 2-pixel width resize template circuit 6 receives pixel data represented by the hatched squares, i.e., points (4,D), (6,D), (4,F), and (6,F), and calculates and outputs a logical OR product of the input data. Whenever the reference image information of logic "1" is input to one of the positions corresponding to these four points, an output 122 of logic "1" appears at the output terminal of the template circuit 6. The output 122 is sent to the processor 15.

Figure 6:
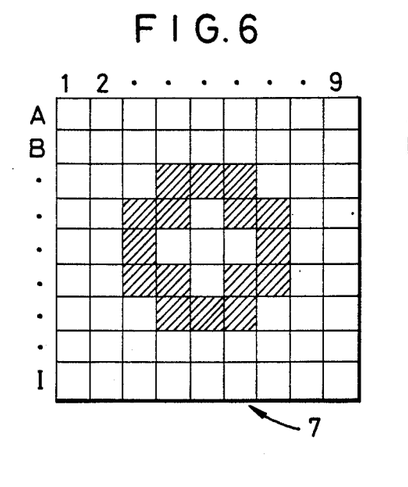

As shown in FIG. 6, the 4-pixel width resize template circuit 7 receives pixel data represented by 16 hatched squares and included in the extracted local image data 104 and calculates and outputs a logical OR product of the input data. Whenever the reference image information of logic "1" is input to any one of positions corresponding to these 16 points, an output 123 of logic "1" appears at the output terminal of the template circuit 7. The output 123 is sent to the processor 15.

Figure 7:
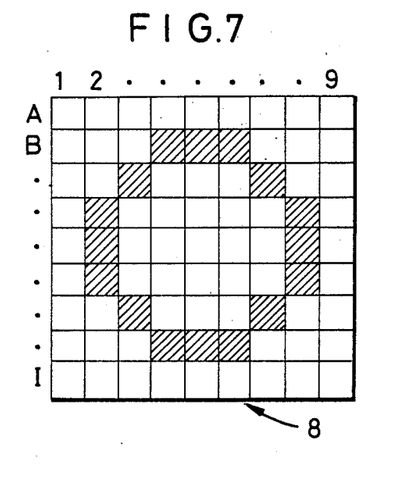

As shown in FIG. 7, the 6-pixel width resize template circuit 8 receives pixel data represented by 16 hatched squares and included in the extracted local image data 104, and calculates and outputs a logical OR product of the input data. Whenever the reference image information of logic "1" is input to any one of positions corresponding to these 16 points, an output 124 of logic "1" appears at the output terminal of the template circuit 8. The output 124 is sent to the processor 15.

Figure 8:
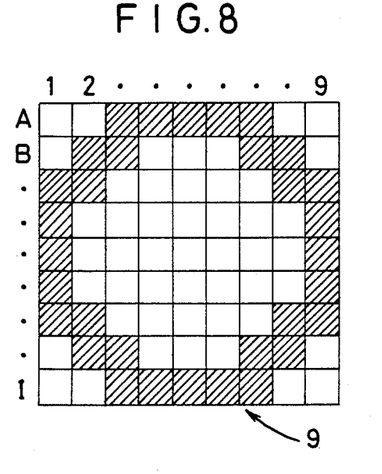

As shown in FIG. 8, the 8-pixel width resize template circuit 9 receives pixel data represented by 32 hatched squares and included in the extracted local image data 104, and calculates and outputs a logical OR product of the input data. Whenever the reference image information of logic "1" is input to any one of positions corresponding to these 32 points, an output 125 of logic "1" appears at the output terminal of the template circuit 9. The output 125 is sent to the processor 15.

Figure 9:
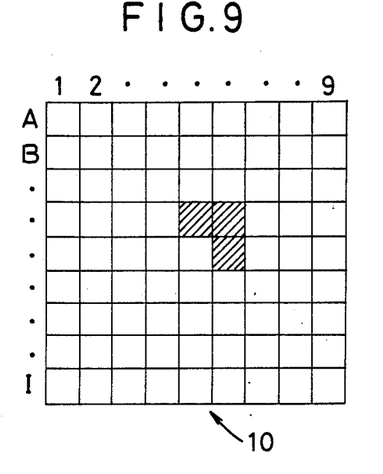

As shown in FIG. 9, the one-pixel width resize template circuit 10 receives pixel data represented by three hatched squares and included in the extracted local image data 104, and calculates and outputs a logical OR product of the input data. Whenever the reference image information of logic "1" is input to any one of positions corresponding to these three points, an output 126 of logic "1" appears at the output terminal of the template circuit 10. The output 126 is sent to the processor 15.

Figure 10:
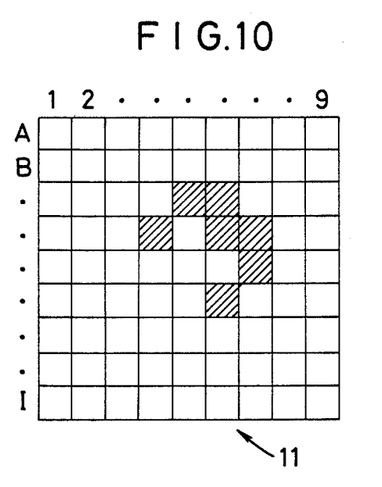

As shown in FIG. 10, the 3-pixel width resize template circuit 11 receives pixel data represented by seven hatched squares and included in the extracted local image data 104, and calculates and outputs a logical OR product of the input data. Whenever the reference image information of logic "1" is input to any one of positions corresponding to these seven points, an output 127 of logic "1" appears at the output terminal of the template circuit 11. The output 127 is sent to the processor 15.

Figure 11:
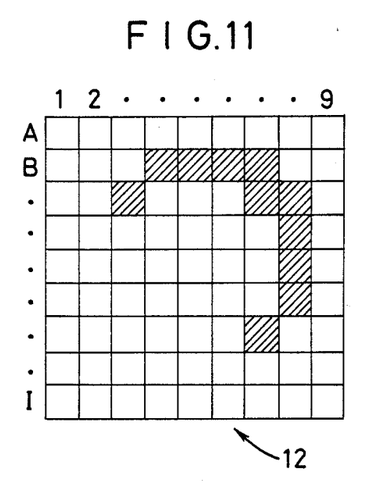

As shown in FIG. 11, the 5-pixel width resize template circuit 12 receives pixel data represented by 11 hatched squares and included in the extracted local image data 104, and calculates and outputs a logical OR product of the input data. Whenever the reference image information of logic "1" is input to any one of positions corresponding to these 11 points, an output 128 of logic "1" appears at the output terminal of the template circuit 12. The output 128 is sent to the processor 15.

Figure 12:
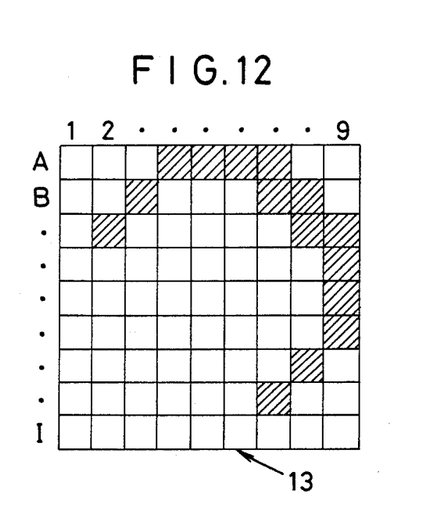

As shown in FIG. 12, the 7-pixel width resize template circuit 13 receives pixel data represented by 15 hatched squares and included in the extracted local image data 104, and calculates and outputs a logical OR product of the input data. Whenever the reference image information of logic "1" is input to any one of positions corresponding to these 15 points, an output 129 of logic "1" appears at the output terminal of the template circuit 13. The output 129 is sent to the processor 15.

The detector 14 for extracting the original image data extracts image data input to a position corresponding to a central pixel, i.e., point (5,E) and outputs extracted data as an output signal 140. The output signal 140 is input to the processor 15.

The processor 15 resizes the pattern on the basis of the outputs 121 to 129 from the template circuits 5 to 13 and the output signal 140 from the detector 14. The processor 15 performs one of the processing modes in response to a selection control signal 161 obtained in correspondence with the command signal COM supplied from the computer 55 to a control section 16. In the first processing mode, the processor 15 cannot perform pattern resizing. In the first processing mode, the processor 15 selects the output signal 140 from the detector 14 and outputs it as output data 150. In the second processing mode, the processor 15 resizes the pattern in the following manner. When 2-pixel width resizing is to be performed, the processor 15 selects the output 140 from the detector 14 and the outputs 121 and 122 from the template circuits 5 and 6, and calculates a logical OR product of the input data. This logical OR product is output as the output data 150.

When 4-pixel width resizing is to be performed, the processor 15 selects the output 140 and the outputs 121 and 123 form the template circuits 5 and 7, and calculates a logical OR product of these input signals. This logical OR product is output as the output data 150.

When 6- or 8-pixel width resizing is to be performed, the processor 15 selects the output 140 and the outputs 121, 123 and 124 or the outputs 121, 123, 124 and 125, and calculates a logic OR product of the four or five inputs. The logical OR product is output as the output data 150.

When one-pixel width resizing is to be performed, the processor 15 selects the output 140 and the output 126 from the template circuit 10 and calculates a logical OR product thereof. The logical OR product is output as the output data 150.

When 3-, 5-, or 7-pixel width resizing is to be performed, the processor 15 receives the output 140 and the outputs 121 and 127 from the template circuits 5 and 11, or the outputs 121, 123, and 128 from the template circuits 5, 7, and 12, or the outputs 121, 123, 124, and 129 from the template circuits 5, 7, 8, and 13, and calculates a logical OR product of these input signals. The logical OR product is output as the output data 150.

The output data 150 is sent as output information 200 through a switching circuit 17.

Figure 13:
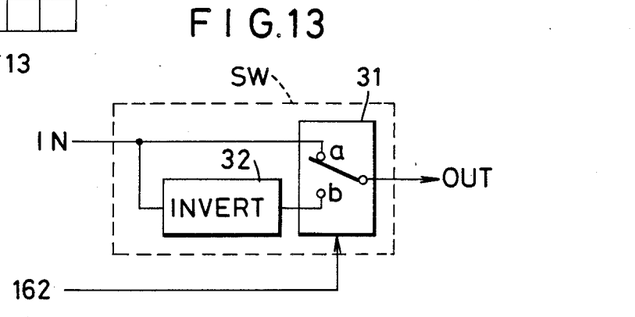
FIG. 13 is a circuit diagram of a switching circuit.

The switching circuits 2 and 17 are arranged to select pattern enlargement and reduction resizing, respectively. For example, a switching circuit SW in FIG. 13 can be employed. The switching circuit SW includes a switch 31 which is operated in response to a switching signal 162 sent from the control section 16. In the enlargement mode, the switch 31 is switched to a noninverting output terminal a, so that an input signal IN is output as an output signal OUT without modification. However, in the reduction mode, the switch 31 is switched to an inverting output terminal b. In this case, the input signal IN is inverted by an inverter 32 to have an inverted logic level, and the inverted signal is output as the output signal OUT.

The computer 55 compares the reference image information with the image information to be inspected to determine how many pixels correspond to a difference between the patterns represented by the reference image information and the image information to be inspected. According to this determination result, the computer 55 switches the command signal COM. The enlargement or reduction ratio for the pattern to be inspected during the fabrication is substantially uniform throughout the pattern. The measurement of the difference can be achieved by a measurement at one location. In response to the command signal COM, the control section 16 generates a selection control signal 161 for causing the processor 15 to select resizing corresponding to the difference between the reference pattern and the pattern to be inspected. For example, if the difference is a 3-pixel difference, a 3-pixel resizing output, i.e., a logical OR product of the output 140 from the detector 14 and the outputs 121 and 127 from the 2- and 3-pixel width resizing template circuits 5 and 11 is selected as the output data 150.

The operation of the apparatus of this embodiment will now be described.

For the sake of simplicity, assume that one of time-serially input reference image information 102 is set at logic "1", that is, assume that the reference image information 102 represents a 1×1 pixel pattern. Also assume that the bit of logic "1" sequentially raster-scans the bits of the pattern memory section 3 having a capacity of 512×8 bits. Processing for inhibiting resizing of the reference image information 102, processing for performing 4-pixel enlargement thereof, and processing for performing 3-pixel enlargement thereof will be described below.

Figure 14:
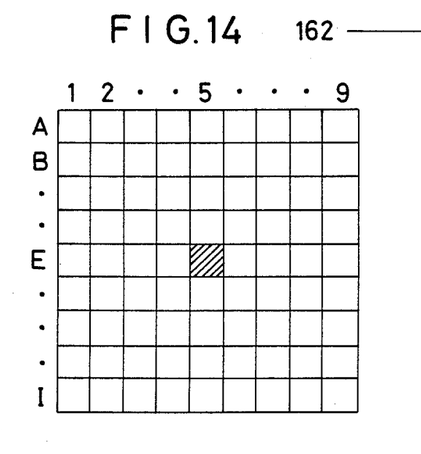
FIG. 14 is a chart showing a reference pattern before resizing.

Processing for inhibiting resizing will be described first. In this case, the processor 15 selects only the output 140 from the detector 14 in response to the selection control signal 161 from the control section 16. The output 140 appears as the output data 150. As a result, a template shown in FIG. 14 can be applied to the reference image information. Referring to FIG. 14, when one-bit reference image information passes through the hatched position corresponding to point (5,E), the output data 150 of logic "1" is output from the processor 15. Output information 200 is stored in a memory which is operated to extract the data in units of local rectangular areas in the same manner as in the extraction section 4. A pixel at a position where a bit of logic "1" appears can be visualized by hatching, as shown in FIG. 14. As is apparent from FIG. 14, the reference image information of 1×1 pixel is expressed as a one-pixel pattern as the central pixel without being modified.

Figure 15:
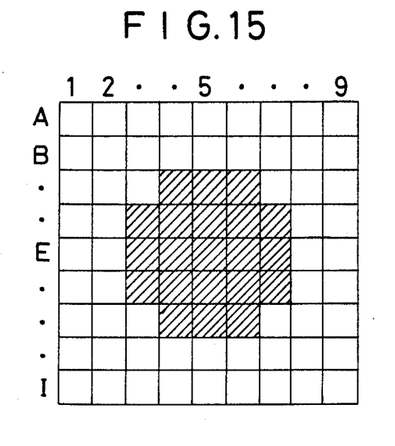
FIG. 15 shows a composite template for 4-pixel

When 4-pixel enlargement is selected, processor 15 selects the output 140 from the detector 14 and the outputs 121 and 123 from the 2- and 4-pixel width resize template circuits 5 and 7, and calculates a logical OR product of these three inputs. The logical OR product is output as the output data 150. As a result, a composite template shown in FIG. 15 can be applied to the reference image information. Referring to FIG. 15, when the one-bit reference image information passes through any one of the hatched positions corresponding to pixel points, the output of logic "1" is generated as the data 150 by the processor 15. Therefore, output information 200 is stored again in the same memory as the extraction section 4. When the pixel at the position where a bit of logic "1" appears is visualized by hatching, the same pattern as in FIG. 15 can be obtained. In practice, the pattern is rotated through 180° for the same reason as in FIGS. 3A and 3B. However, the pattern in FIG. 15 is symmetrical about its center. As a result, no change appears in this pattern. As is apparent from the comparison with the case of FIG. 14, the original image pattern is enlarged by two pixels in all directions with respect to the central pixel represented by point (5,E) corresponding to the original image data.

Figure 16:
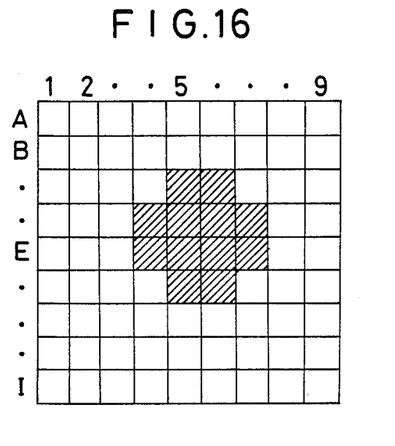
FIG. 16 shows a composite template for 3-pixel width resizing.
Figure 17:
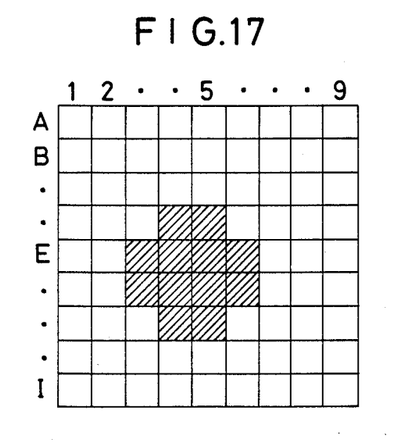
FIGS. 17 and 18 show patterns after 3-pixel enlargement.

When 3-pixel enlargement is selected, the processor 15 selects the output 140 from the 2- and 3-pixel width resize template circuits 5 and 11, and calculates a logical OR product of these three inputs. The logical OR product is output as the output data 150. As a result, a composite template shown in FIG. 16 can be applied to the reference image information. Referring to FIG. 16, when the one-bit reference image information passes through any one of the hatched positions corresponding to pixel points, the output of logic "1" is generated as the data 150 by the processor 15. Therefore, output information 200 is stored again in the same memory as the extraction section 4. When the pixel at the position where a bit of logic "1" appears is visualized by hatching, the same pattern as in FIG. 17 can be obtained. In practice, the pattern in FIG. 17 is rotated through 180° with respect to the pattern of FIG. 16 for the same reason as in FIGS. 3A and 3B. As is apparent from the comparison with the case of FIG. 14, the original image pattern is enlarged by two pixels at the left and lower sides with respect to the central pixel represented by point (5,E) corresponding to the original image data. The original image pattern is enlarged by one pixel at the right and upper sides.

Figure 18:
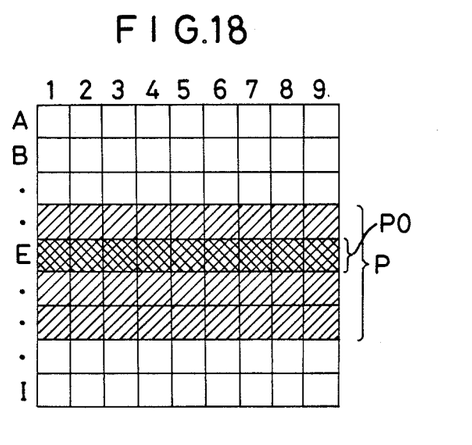

3-pixel enlargement processing generates, for example, a reference pattern P obtained by enlarging a linear pattern P0 by two pixels at the lower side and one pixel at the upper side as shown in FIG. 18. In this case, the linear pattern P0 has a width of one pixel and consists of points (1,E) to (9,E).

In the size reduction mode wherein a pattern represented by reference image information 100 is to be reduced, the switching circuits 2 and 17 are switched to the reduction terminal b in response to the selection control signal 161 of the control section 16. The switching circuit 2 inverts the logic levels of the reference image information and outputs the inverted logic levels as reference image information 102. The reference image information 102 is processed in the same manner as in the enlargement mode. Thereafter, the logic levels of the output data 150 from the processor 15 are inverted again by the switching circuit 17 and the again inverted logic levels appear as output information 200.

Figure 19:
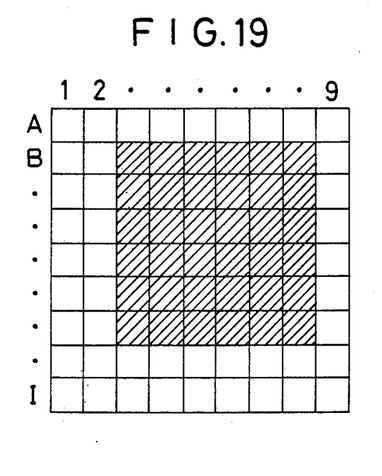
FIG. 19 shows a reference pattern before size reduction.
Figure 20:
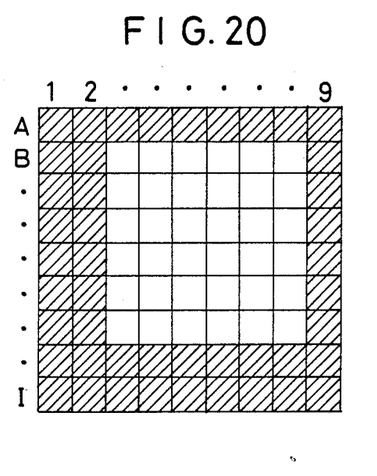
FIG. 20 shows an inverted pattern generated by size reduction.
Figure 21:
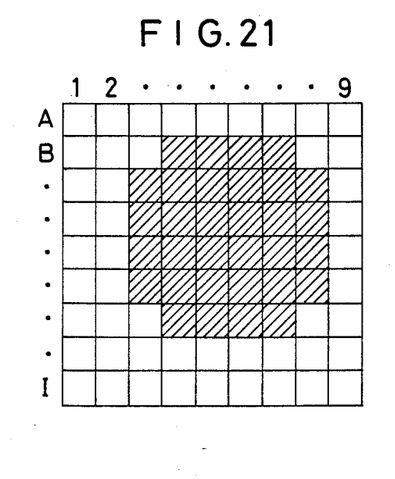
FIG. 21 shows a composite template for 5-pixel width resizing.

For example, if the reference image information 100 corresponding to the reference pattern of 6×6 pixels of logic "1", as shown in FIG. 19, is input to the apparatus and the pattern to be inspected corresponding to the image information is a 1×1 pixel pattern in FIG. 14, a difference between these patterns corresponds to 5 pixels along the horizontal and vertical directions. In order to match the reference pattern with the pattern to be inspected, the reference pattern must be reduced by 5 pixels. The reference image information 102 is inverted by the switching circuit 2 to obtain a pattern including inner 6×6 white pixels, as shown in FIG. 20. The resultant reference image information 102 is input to the corresponding template circuits through the extraction circuit 4. The processor 15 selects the output 140 from the detector 14 and the outputs 121, 123, and 128 from the 2-, 4-, and 5-pixel width resize template circuits 5, 7, and 12 and calculates a logical OR product of these four inputs. The logical OR product appears as the output data 150. Therefore, a composite template shown in FIG. 21 can be applied to the reference image information. The output information 200 obtained by inverting the output 150 through the switching circuit 17 is stored in the memory. When the pixel at the position where a bit of logic "1" appears is visualized by hatching, the resultant pattern is given as the one of logic "1" located at the central pixel represented by pixel (5,E) and corresponds to the size of the pattern to be inspected.

According to the pattern resize circuit 1 of this embodiment, the pattern is enlarged or reduced as needed to provide the output information 200.

The template circuits 5–13 can comprise logic circuits using P-ROMs, PALs, and the like.

According to this embodiment, even if the difference between the reference pattern and the pattern to be inspected is an odd number, optimal enlargement or reduction can be performed. As is apparent from the comparison with reference to FIGS. 14 and 17, the center of the pattern prior to resizing in FIG. 14 is the one of the pixel represented by point (5,E). The center of the pattern after resizing in FIG. 17 is shifted to the lower left vertex of the pixel represented by point (5,E). The center of the pattern prior to resizing in FIG. 19 is the upper right vertex of the pixel represented by point (5,E). However, the center of the pattern after resizing is the one of the pixel represented by point (5,E). Therefore, if resizing of odd-numbered pixel width is performed, the shift direction of the center of the pattern is always the lower left direction, i.e., a 45° direction with respect to the center. The template circuits are arranged such that the shift amount is 0.5 pixel in the left or lower direction. The shift direction and amount of the reference pattern after resizing are thus standardized. In order to cause the inspecting circuit 54 to guarantee synchronization between the reference image information and the image information to be inspected, the stage 51 is driven to provide a predetermined offset to the relative position between the pattern to be inspected and the image pick-up device 52, thereby matching between the reference pattern and the pattern to be inspected.

What is claimed is:

1. A pattern inspection apparatus for inspecting a pattern formed on a substrate on the basis of design information, the pattern on the substrate having dimensional tolerances with respect to size of the pattern represented by said design information, comprising:

means for picking up a pattern formed on the basis of design information and generating image data corresponding to a local area of the pattern;

means for extracting reference information required for forming a pattern within the local area from the design information, the reference information being expressed by logic levels of pixels corresponding to the pattern within the local area;

template means for receiving the reference information and detecting that a predetermined logic level is present at a predetermined position when a pixel logic level distribution is applied to the local area;

resizing means for combining additional information represented by a logic level corresponding to said dimensional tolerances to the pixel at the predetermined position of the reference information in response to said template means so that the size of the pattern represented by said reference information may be coincident with the size of the pattern on the substrate;

said resizing means shifting one edge of a pair of edges determining a width in a predetermined direction of the local area pattern represented by said reference information by an amount corresponding to an odd number times the pixel size and shifting the other edge of said pair of edges by an amount corresponding to zero or an even number times the pixel size; and means for comparing the resized reference information with the image data.

2. An apparatus according to claim 1, wherein said template means detects the logic levels of pixels adjacent to the pixel of the predetermined position which is combined with the additional information by said resizing means.

3. An apparatus according to claim 1, wherein the image data constituting the pattern in the local area is represented by a binary logical level, said image data generating means includes first output switching means having a mode for inverting the binary logic level of the image data and outputting inverted data and a mode for outputting the image data without inverting the binary logic level thereof, and said resizing means includes second output switching means having a mode for inverting a logic level of the resized reference information and outputting the inverted resized reference information and a mode for outputting the resized reference information without inversion, said first and second output switching means being synchronized.

4. An apparatus according to claim 1, wherein said template means includes means for inputting logic levels of plural pixels selected within said local area and calculating an output logical OR product.

5. A pattern inspection apparatus comprising:

means for picking up a pattern formed on the basis of design information and generating image data corresponding to a local area of the pattern;

means for extracting reference information required for forming a pattern within the local area from the design information, the reference information being expressed by logic levels of pixels corresponding to the pattern within the local area;

means for resizing the pattern represented by the reference information, said resizing means being adapted to resize the reference information so as to shift respective positions of edges of said local area pattern by different amounts, the edges determining a width in a predetermined direction of the local area pattern represented by the reference information;

said resizing means shifting one of said edges by an amount corresponding to an odd number times the pixel size and shifting another of said edges by an amount corresponding to zero or an even number times the pixel size; and means for comparing the resized reference information with the image data.

* * * * *